(12) United States Patent
Stucki (10) Patent No.: US 7,597,309 B1
(45) Date of Patent: Oct. 6, 2009

(54) CONSTANT-RATE VOLATILE MATERIAL DISPENSING DEVICE

(76) Inventor: Andre Stucki, 349 SE. 2nd Ave., Deerfield Beach, FL (US) 33441

( * ) Notice: Subject to any disclaimer, the term of this patent is extended or adjusted under 35 U.S.C. 154(b) by 0 days.

(21) Appl. No.: 12/199,527

(22) Filed: Aug. 27, 2008

Related U.S. Application Data (63) Continuation-in-part of application No. 11/786,287, filed on Apr. 11, 2007.

(60) Provisional application No. 60/791,133, filed on Apr. 11, 2006.

(51) Int. Cl.
B01F 3/04 (2006.01)

(52) U.S. Cl. ............... 261/30; 222/96; 222/187; 361/37; 361/104; 361/DIG. 88

(58) Field of Classification Search ............ 261/30, 261/34.1, 37, 66, 71, 104, 107, DIG. 17, 261/DIG. 65, DIG. 88, DIG. 89; 222/3, 95, 222/96, 187; 239/53–56; 422/5, 28, 122–124
See application file for complete search history.

(56) References Cited

U.S. PATENT DOCUMENTS

| | | | |
|---|---|---|---|
| 3,892,235 A * | 7/1975 | Van Amerongen et al. | 128/200.16 |
| 3,982,095 A * | 9/1976 | Robinson | 392/403 |
| 4,051,205 A * | 9/1977 | Grant | 261/70 |
| 4,225,542 A * | 9/1980 | Wall et al. | 261/142 |
| 4,288,396 A * | 9/1981 | Ottestad | 261/128 |
| 4,367,182 A * | 1/1983 | Kienholz | 261/124 |
| 4,461,735 A * | 7/1984 | Wirt | 261/104 |
| 4,657,713 A * | 4/1987 | Miller | 261/142 |
| 4,739,928 A * | 4/1988 | O'Neil | 239/45 |
| 4,752,422 A * | 6/1988 | Uchida et al. | 261/81 |
| 5,000,383 A * | 3/1991 | van der Heijden | 239/47 |
| 5,238,187 A * | 8/1993 | Zlotnik et al. | 239/6 |
| 5,247,604 A * | 9/1993 | Chiu | 392/406 |
| 5,361,322 A * | 11/1994 | Glucksman | 392/405 |
| 6,511,531 B1 * | 1/2003 | Cartellone | 96/222 |
| 6,523,810 B2 * | 2/2003 | Offir et al. | 261/72.1 |
| 6,869,065 B1 * | 3/2005 | Lin | 261/3 |
| 7,040,548 B2 * | 5/2006 | Rodgers | 239/34 |
| 2002/0158351 A1 * | 10/2002 | Wohrle | 261/142 |
| 2004/0099967 A1 * | 5/2004 | Chen | 261/66 |

FOREIGN PATENT DOCUMENTS

| | | | | | |
|---|---|---|---|---|---|
| JP | 54-98034 A | * | 8/1979 | | 261/DIG. 17 |
| JP | 5-52371 A | * | 3/1993 | | 261/DIG. 65 |

* cited by examiner

*Primary Examiner*—Richard L Chiesa
(74) *Attorney, Agent, or Firm*—Gold & Rizvi, P.A.; H. John Rizvi; Glenn E. Gold (57) ABSTRACT

A volatile material dispensing device is provided, including a volatile material, a replaceable canister including a U-shaped outlet tube and a reservoir to hold the volatile material, and a generally cylindrical external housing sized and configured to receive the replaceable canister. The U-shaped outlet tube includes a tube inner leg, a tube crosspiece, and a tube outer leg, with the tube inner leg fluidly connected to the cavity and with the tube outer leg open to the atmosphere. The external housing includes a powered actuating unit configured to apply pressure to the flexible outer wall of the reservoir. Thereby a portion of the volatile material is forced up the inner tube, over the tube crosspiece, and down the outer tube to be received by a porous pad, providing a time-release dispersing mechanism delivering a controlled, consistent flow and producing a constant intensity of vapor release over time.

24 Claims, 7 Drawing Sheets

CONSTANT-RATE VOLATILE MATERIAL DISPENSING DEVICE

CROSS-REFERENCE TO RELATED APPLICATIONS

This application claims the benefit of co-pending U.S. Non-Provisional patent application Ser. No. 11/786,287 filed Apr. 11, 2007, which takes priority from Provisional Patent Application Ser. No. 60/791,133 filed Apr. 11, 2006, which are incorporated by reference herein in their entirety.

BACKGROUND OF THE INVENTION

1. Field of the Invention

The present invention relates generally to volatile material dispensing devices such as air freshener dispensers, and more particularly, to a volatile material dispensing device for dispensing the volatile material from a replaceable canister at a constant rate.

2. Description of the Prior Art

A number of attempts have been made to devise volatile material dispensing devices. These devices commonly dispense perfumed fluid, aromatic oils, odor deodorizers, or scented gels that scent the atmosphere. Typically these devices are used in a room, vehicle, or other confined space.

Volatile material dispensing devices that are designed to produce a pleasing aroma, often called air fresheners, have become common household products. Not only do these provide a sense of cleanliness and pleasantness, but they also offer the benefit of increased safety. For example, some universities do not allow the use of candles in dormitory rooms due to danger from fire, but encourage the use of safe and effective volatile material air fresheners instead.

Various systems of dispersal are known, both active and passive.

Active systems include both manual systems and powered systems. Manual systems function when a button is pushed to activate the dispersal mechanism, such as when the button is depressed on an aerosol can. By quickly spraying a quantity of small particulates, manual systems have the advantage of fast delivery, however they do not provide automatic, continuous dispersal, but require initiation by the consumer each time dispensing is desired. Powered systems, using electricity or battery power, promote the diffusion of the vapor into the atmosphere by heating the volatile material, or by increasing air circulation and turbulence around the volatile material via a fan mechanism. Active powered systems, while automatically providing continuous dispersal, do not provide a constant level of intensity. They initially provide a higher intensity that diminishes as time passes, as demonstrated in FIG. 1. Even on the Glade® website, a popular manufacturer of electrically warmed scented oils, the FAQ page informs its customers to expect that the fragrance will be stronger the first few days.

Figure 1:
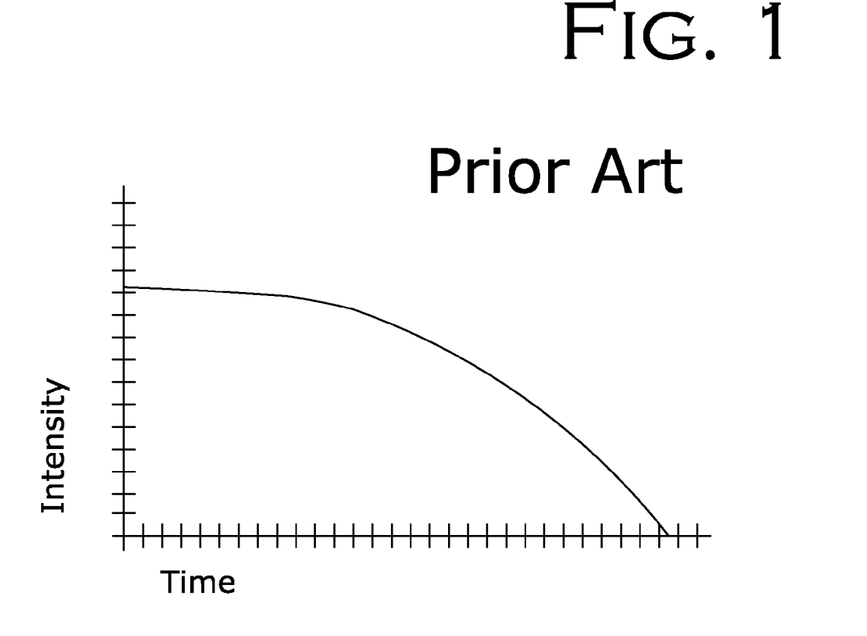
FIG. 1 is a graph demonstrating the varying, diminishing intensity of vapor release of prior art devices showing vapor intensity versus time.

Various passive types of volatile material dispensing devices are known. Some early types called inverted bottle evaporators used a gravity-fed system. A bottle filled with the liquid was inverted in a pan to allow a pool of the liquid to form in the pan. Evaporation occurred from the pool surrounding the neck of the bottle. This type was so prone to spills that it is no longer commercially available. Some other older types, which are still offered, employ a container of an aromatic liquid or oil that is open to the air. Often a wick is provided to increase the surface area available for evaporation. These too are messy, prone to spillage, and potentially hazardous to children and pets that might access the open container. Furthermore, the intensity fades over time, due to the reduction in the amount of the aromatic liquid available for evaporation. Aromatic gels or semi-solids were more recently introduced. Gels are often enclosed in a vapor-permeable material and formed into a convenient, disposable cartridge. Other disposable cartridges include pads or sponge-like material permeated with vaporizable agents. The cartridges are less cumbersome and more convenient, but the scent is short lived, necessitating frequent replacement. Additionally, disposable cartridges are not able to provide a constant level of intensity over time; instead the high initial intensity drops off quickly, as shown in FIG. 1.

Accordingly, there is an established need for a convenient volatile material dispensing device that is capable of delivering a controlled, consistent flow, producing a constant intensity of vapor over time.

SUMMARY OF THE INVENTION

The present invention is directed to an improved volatile material dispensing device that is capable of delivering a controlled, consistent flow, with an appropriate drip rate to produce a constant intensity of vapor over time. The volatile material dispensing device includes a supply of any of numerous volatile materials, a replaceable canister comprising a U-shaped outlet tube 35 and a reservoir to hold the volatile material, and a generally cylindrical external housing sized and configured to receive and/or hold the replaceable canister.

The U-shaped outlet tube 35 comprises a tube inner leg, an upper tube crosspiece, and a tube outer leg, with the tube inner leg fluidly connected to the cavity and with the tube outer leg open to the atmosphere.

The external housing comprises a powered actuating unit configured to apply pressure to the flexible outer wall of the reservoir. This pressure forces a small portion of the volatile material out of the reservoir and into the bottom of the inner tube, up the inner tube, and over the upper tube crosspiece and down the outer tube for release out of the bottom of the outer tube where the volatile material is preferably received by a absorbent pad; thus providing a time-release dispersing mechanism.

The external housing preferably is configured with air passageways and comprises a fan to aid in atmospheric dispersal of the volatile material. The external housing also preferably comprises a lid configured with air passageways.

The absorbent pad is optionally affixed to the external housing or to the replaceable canister.

The volatile material dispensing device preferably includes a tear-off tab that initially seals the outer leg of the U-shaped tube and prevents the flow of the volatile material until the tab is removed by the consumer to activate the system and initiate the flow.

An object of the present invention is to present a volatile material dispensing device that provides a consistent and appropriate volatile material drip rate.

Another object of the present invention is to present a volatile material dispensing device that provides a consistent, appropriate, and constant volatile material dispersal rate, to provide a constant intensity of vapor over time.

Another object of the present invention is to provide a volatile material dispensing device that is relatively inexpensive to manufacture.

An additional object of the present invention is to provide a volatile material dispensing device that can be adapted for use with a wide variety of volatile materials.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Figure 2:
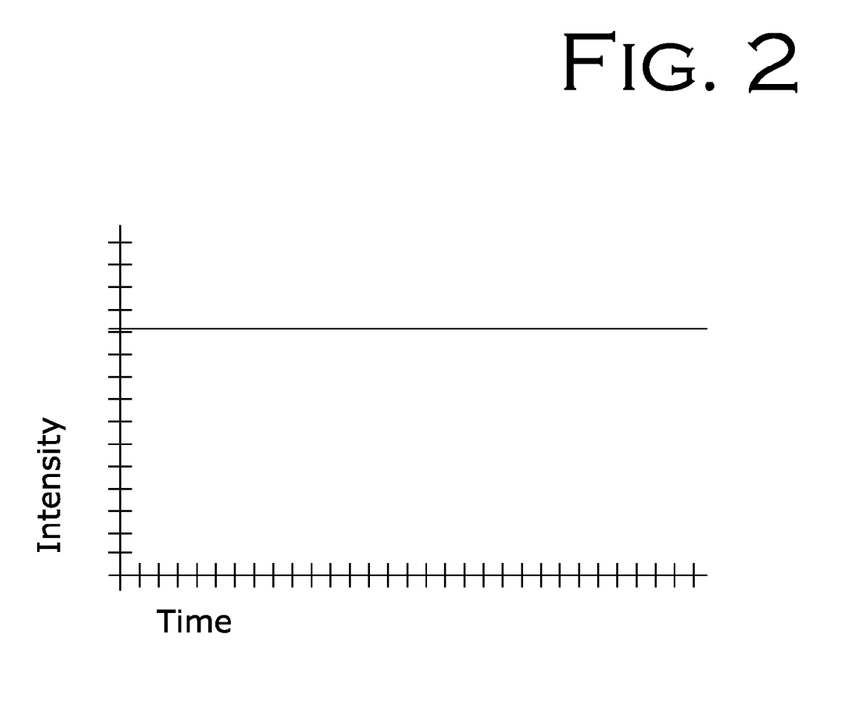
FIG. 2 is a graph demonstrating the constant intensity of vapor release of the volatile material dispensing device of the present invention showing vapor intensity versus time.

Shown throughout the figures, the present invention is directed towards an improved, effective, and convenient volatile material dispensing device. Whereas previous devices exhibited varying, decreasing vapor intensity over time as demonstrated in FIG. 1, the present improved volatile material dispensing device provides constant vapor intensity over time, as shown in FIG. 2, by utilizing a time-release dispensing mechanism delivering a controlled, consistent flow, with an appropriate drip rate.

Figures 3, 4:
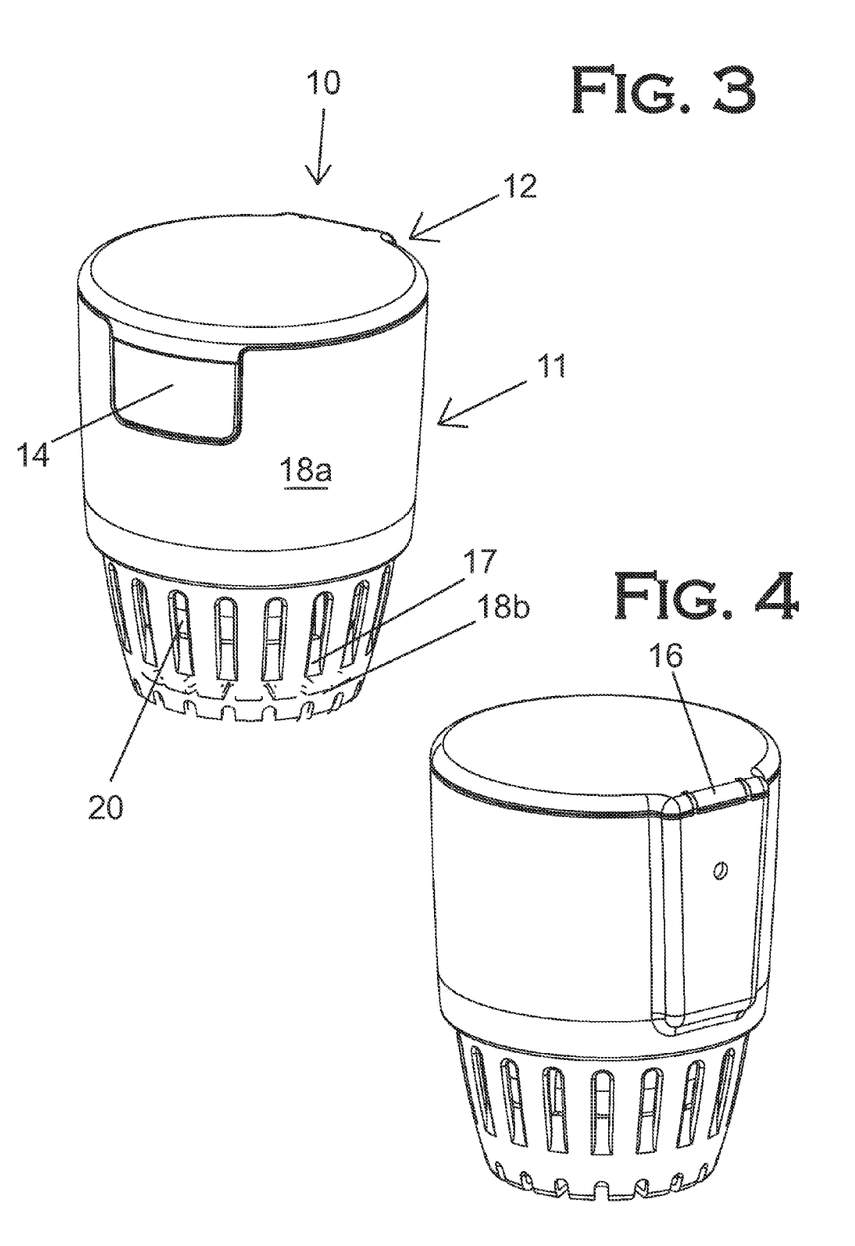
FIG. 3 is a front perspective view showing a first preferred embodiment of the volatile material dispensing device of the present invention.
FIG. 4 is a back perspective view showing the first preferred embodiment of the volatile material dispensing device of the present invention.
Figure 7:
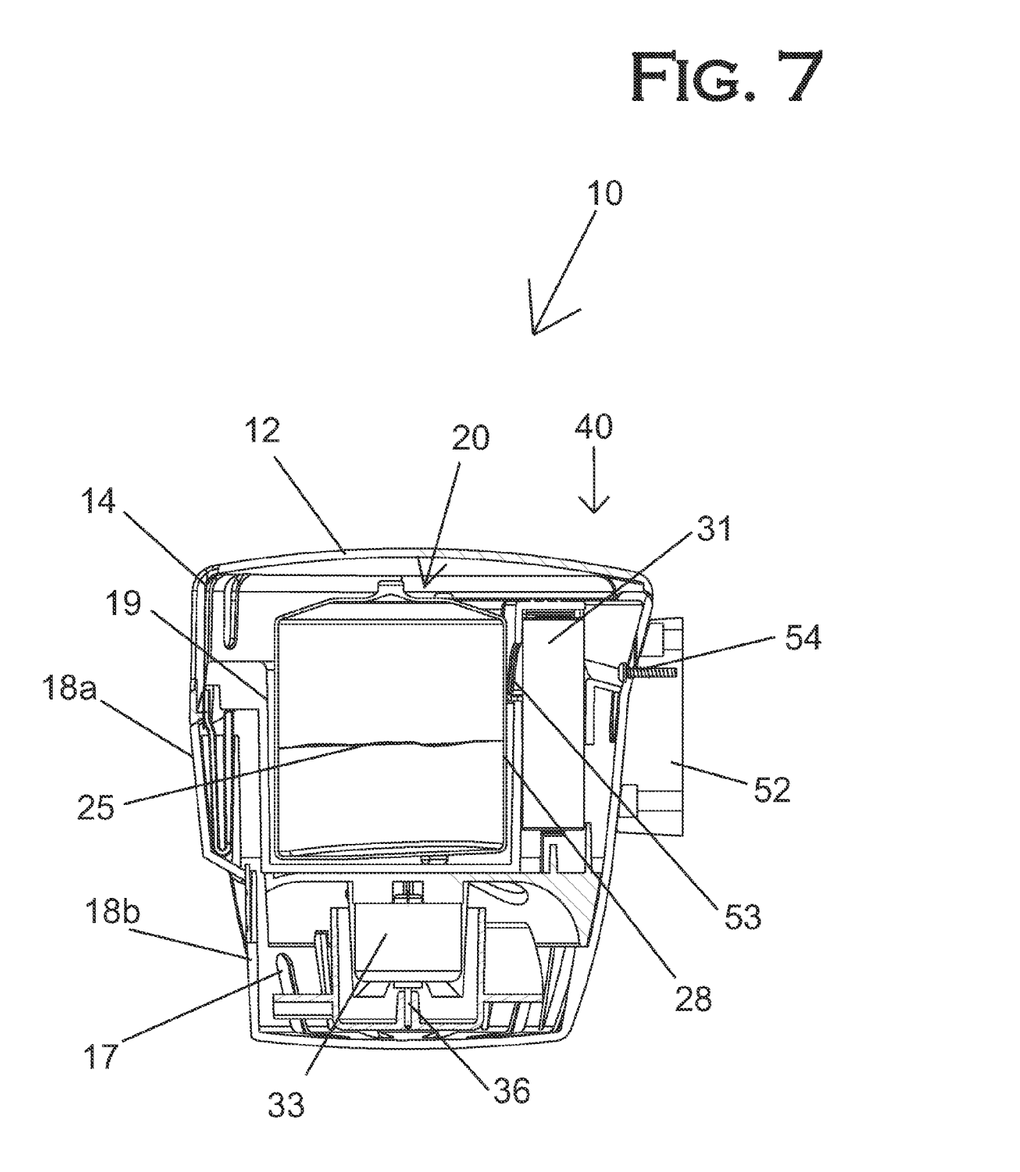
FIG. 7 is a cutaway view along the lines of 7-7 of FIG. 6 of the second preferred embodiment of the volatile material dispensing device of the present invention.
Figure 8:
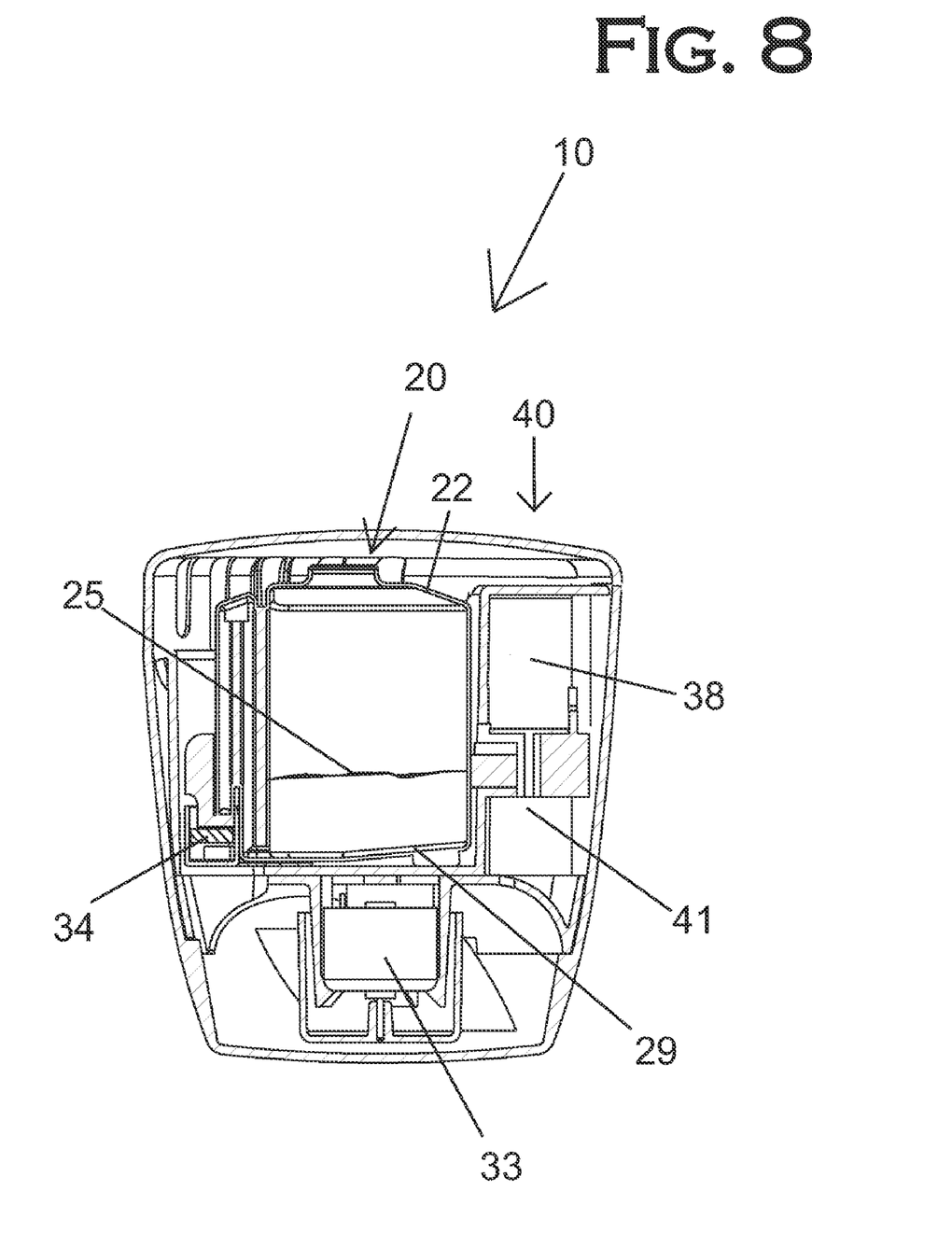
FIG. 8 is a cutaway view along the lines of 8-8 of FIG. 6 of the second preferred embodiment of the volatile material dispensing device of the present invention.
Figures 9, 10:
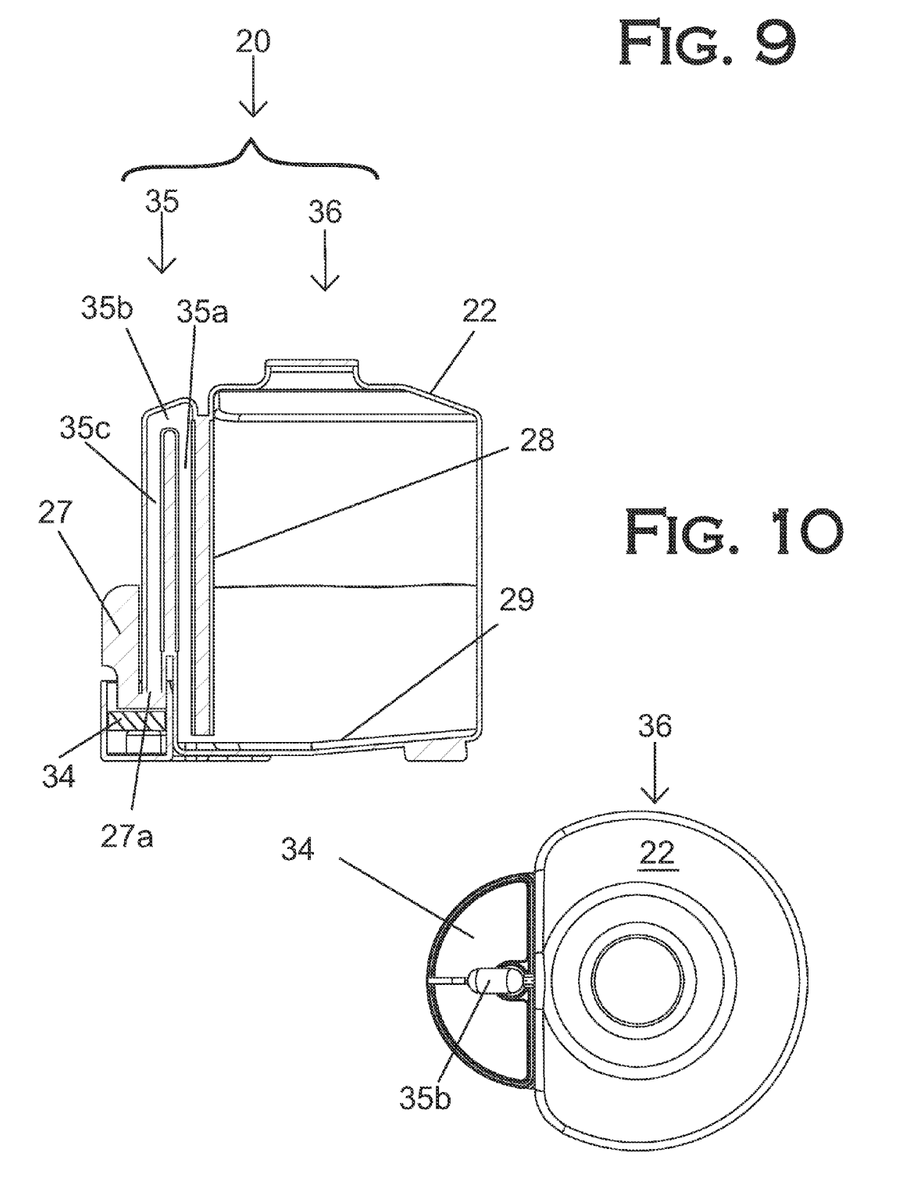
FIG. 9 is a cutaway view along the lines of 7-7 of FIG. 6 of the replaceable canister of the second preferred embodiment of the volatile material dispensing device of the present invention.
FIG. 10 is a top view of the replaceable canister of the second preferred embodiment of the volatile material dispensing device of the present invention.
Figure 11:
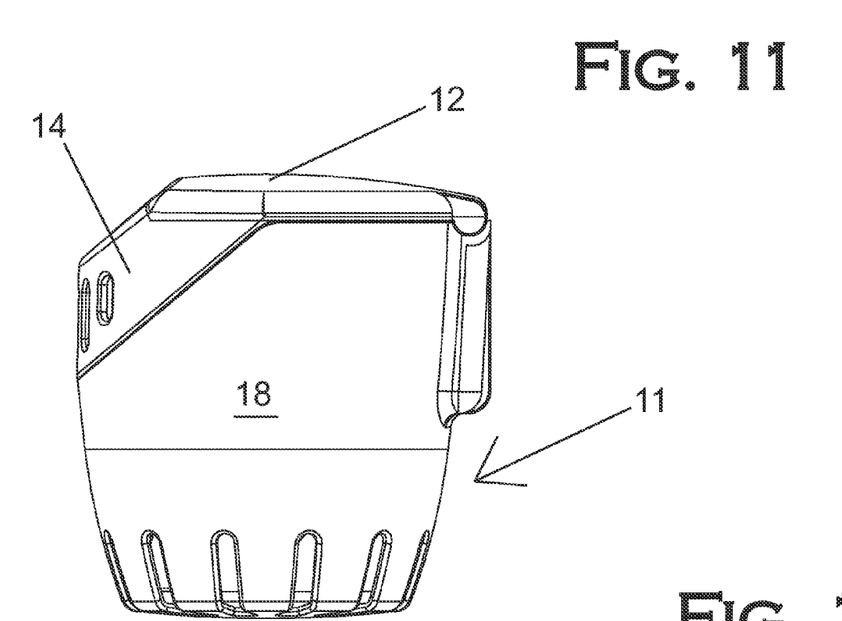
FIG. 11 is a side view of a third preferred embodiment of the volatile material dispensing device of the present invention.
Figure 12:
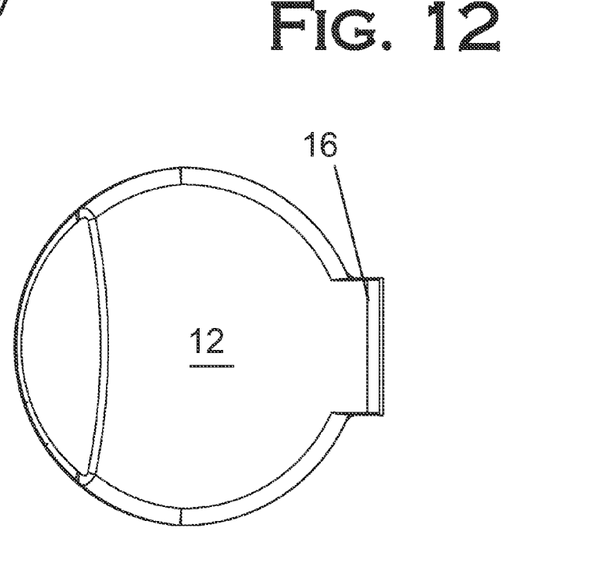
FIG. 12 is a top view of the third preferred embodiment of the volatile material dispensing device of the present invention.

The volatile material dispensing device, shown generally as reference number 10, is illustrated in accordance with a first embodiment of the present invention (FIG. 3, FIG. 4) and a second preferred embodiment of the present invention (FIG. 5 to FIG. 10), and a third embodiment of the present invention (FIG. 11 to FIG. 12). The volatile material dispensing device 10 comprises an external housing 11 and an inner replaceable canister 20 (FIG. 8, FIG. 9), with inner replaceable canister 20 configured to contain a supply of a volatile material 25 (FIG. 8, FIG. 9).

External housing 11 serves as a holder or container for the inner replaceable canister 20. External housing 11 preferably comprises a housing side wall 18, a housing bottom wall 15 (FIG. 5), housing interior surfaces defining a housing interior chamber 19 (FIG. 7), and a powered actuating unit 40 (FIG. 7).

The housing side wall 18 is generally cylindrical. The housing side wall 18 may optionally be formed of two sections as illustrated, upper housing side wall 18a and lower housing side wall 18b, with lower housing side wall 18b being shaped as a slightly tapered cylinder or truncated cone. The bottom edge of housing side wall 18b is joined to the generally circular housing bottom wall 15.

The interior surfaces of external housing 11 define the housing interior chamber 19 that is sized and configured to receive the replaceable canister 20.

Best seen in FIG. 9, FIG. 10, inner replaceable canister 20 comprises a reservoir 36 and a U-shaped outlet tube 35. The U-shaped outlet tube 35 is fluidly connected to a lower area of a reservoir side wall 28 (FIG. 7, FIG. 9).

Referring now to FIG. 7 and FIG. 8, the powered actuating unit 40 is configured to apply pressure to the flexible reservoir side wall 28 of the inner replaceable canister 20. Powered actuating unit 40 comprises an activator 53 operatively configured to apply pressure to the reservoir side wall 28, a motor 41 (FIG. 8), and connective gearing 38 (FIG. 8), to operatively connect the motor 41 to the activator 53 (FIG. 7). The motor 41 is preferably powered by a low voltage power source, either an ac power source such as a step-down transformer, or, more preferably, a dc power source such as a battery 31 (FIG. 7) or solar cell (not shown).

Preferably external housing 11 also comprises a lid 12 (FIG. 3, FIG. 4) connected to an upper area of housing side wall 18 via hinge 16. Lid 12 is generally circular with a small extension 12x (FIG. 6) to allow appropriate connection of hinge 16. Hinge 16 is attached to the rearward edge of lid 12 and to the rearward side of upper housing side wall 18a. Hinge 16 is configured to allow lid 12 to be positioned in a closed position (as shown) or in an open position to allow access to the housing interior chamber 19 for insertion or removal of the inner replaceable canister 20 (FIG. 7-FIG. 9). Optionally, a lid fastener 14 is provided and is attached to the forward edge of lid 12. Lid fastener 14 is configured to lock, catch, latch, or secure lid 12 to an upper, forward area of housing side wall 18.

Lower housing side wall 18b is preferably configured with numerous housing air passageways 17. Housing air passageways 17 are vents configured to allow for air circulation or air turbulence to encourage evaporation of the volatile material. They provide a means by which the aroma from the volatile material 25, held in the interior of the volatile material dispensing device, can exit to the atmosphere. Although upper housing side wall 18a and lower housing side wall 18b are illustrated and discussed as separate sections, the two can equally well be combined into a single wall forming a generally cylindrical housing side wall 18, incorporating the features of both upper housing side wall 18a and lower housing side wall 18b, including hinge 16 and housing air passageways 17.

Figure 5:
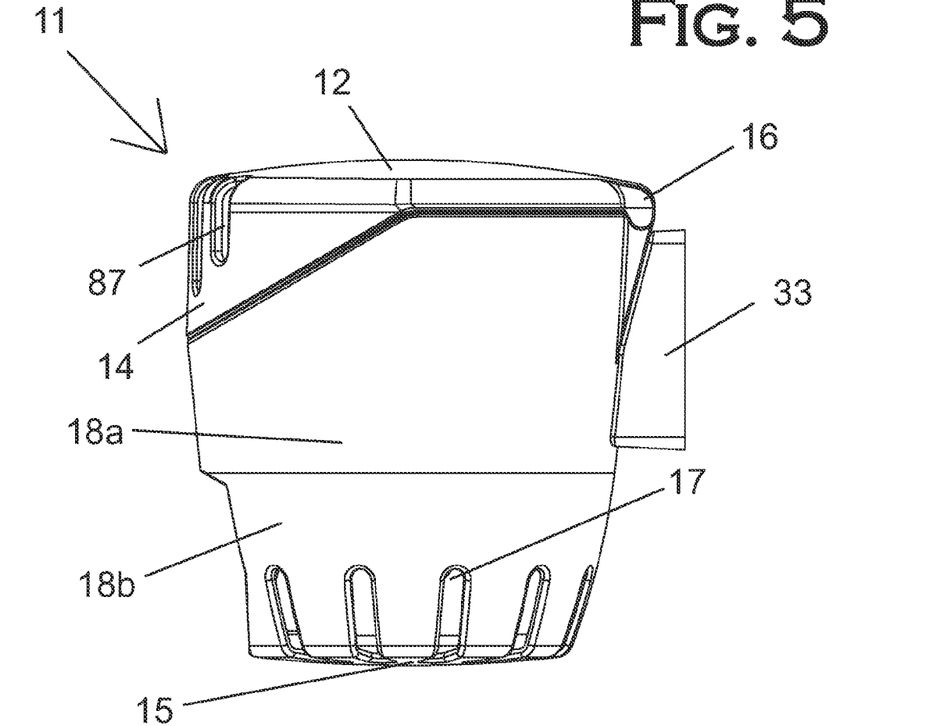
FIG. 5 is a side view of a second preferred embodiment of the volatile material dispensing device of the present invention.
Figure 6:
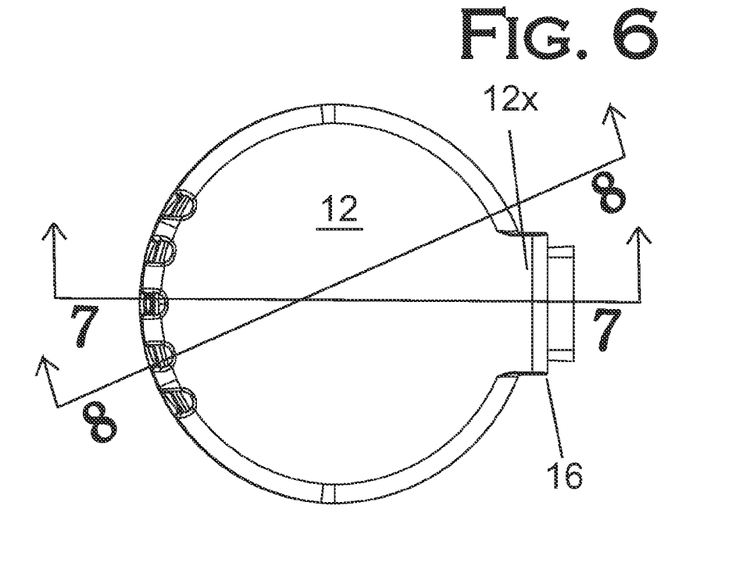
FIG. 6 is a top view of the second preferred embodiment of the volatile material dispensing device of the present invention.

The design of external housing 11, lid 12, lid fastener 14, and housing air passageways 17 may be varied due to considerations of aesthetics, economy of production, and convenience of access to inner replaceable canister 20, as is exemplified by the three embodiments presented. For example, as illustrated in the second embodiment, lid 12 can optionally be configured with one or more lid air passageways 87 (FIG. 5, FIG. 6). Or, for example, as illustrated in the third embodiment (FIG. 11, FIG. 12) the lid may be irregularly formed, such as a vertically truncated cylinder or the air passageways may have any of a wide variety of shapes and/or positions.

Preferably external housing 11 is made of plastic or other synthetic or semi-synthetic polymers or other suitable materials that are lightweight, economical, easy-to-process, and generally rigid.

Referring now to FIG. 9 and FIG. 10, the inner replaceable canister 20 is illustrated as removed from the external housing 11. Inner replaceable canister 20 comprises a reservoir 36 and a U-shaped outlet tube 35.

The reservoir 36 is rounded, being generally in the shape of a partial cylinder or vertically truncated cylinder, as shown (FIG. 10). Reservoir 36 comprises a reservoir top wall 22, a reservoir side wall 28, and a reservoir bottom wall 29, which may be integrally formed or may be joined at the time of manufacture. Most preferably reservoir bottom wall 29 is slightly slanted, as illustrated, to allow optimum flow of volatile material 25 toward U-shaped outlet tube 35.

The inner surfaces of the reservoir top wall 22, reservoir side wall 28, and reservoir bottom wall 29 define an inner reservoir cavity configured to accommodate a supply of any of a number of volatile materials 25, such as perfumed fluid, aromatic oils, volatile organic compounds, aromatherapy scents, odor neutralizers, odor deodorizers, disinfectants, air fresheners, scented gels, insecticides, bioactive materials, or the like, that condition, modify, or otherwise change the atmosphere. Optionally, a combination of more than one of these volatile materials 25 may equally well be utilized in the volatile material dispensing device 10 of the present invention. In the manufacturing process, reservoir 36 is preferably filled with volatile material 25 through top canister wall 22 and then top canister wall 22 is sealed, preferably by a heat seal.

The U-shaped outlet tube 35 (FIG. 9, FIG. 10) comprises a tube inner leg 35a and a tube outer leg 35c joined by an upper tube crosspiece 35b, which together form an open channel through which volatile material 25 can move. The tube inner leg 35a is connected to a lower area of side canister wall 28 and is fluidly connected to the inner reservoir cavity, allowing the volatile material 25 to flow into U-shaped outlet tube 35 in an unrestricted manner.

Reservoir top wall 22, reservoir side wall 28, and reservoir bottom wall 29 are preferably formed or molded of plastic, or other synthetic or semi-synthetic polymer, that is lightweight and easy to process. The reservoir side wall 28 has a degree of flexibility, to allow a degree of deformation when pressure is applied to reservoir side wall 28 via powered actuating unit 40 to encourage a portion of the quantity of volatile material 25 to enter the tube inner leg 35a. The amount of pressure applied by powered actuating unit 40 is sufficient to force the portion of the quantity of volatile material 25 to flow up the tube inner leg 35a and into tube crosspiece 35b, with a small amount then flowing into tube outer leg 35c and downward out the distal end of tube outer leg 35c, where it is received by pad 34.

Pad 34 is impregnated by the volatile material 25 at an appropriate, constant drip rate for optimum dispersal. Then the volatile material 25 evaporates at a steady rate to permeate the atmosphere. The flow rate is continuous over time; therefore the amount of volatile material 25 impregnating pad 34 and evaporating is constant and the intensity of the vapor produced is constant over time, as shown in FIG. 2.

Pad 34 may optionally be replaceable or non-replaceable. If pad 34 is to be replaceable, it is a component of the inner replaceable canister 20 and is attached to an exterior area of side canister wall 28, positioned below the distal end of tube outer leg 35c. If pad 34 is to be non-replaceable, it is a component of the external housing 11, and is disposed within the housing side wall 18, positioned in a location that will be generally centered under the distal end of tube outer leg 35c, when the inner replaceable canister 20 is placed within the external housing 11. Pad 34 may be formed of any porous material, such as foam, woven or non-woven fabric, or any other absorbent material.

Preferably at the time of manufacture, a protective cover 27a (FIG. 9) is placed over the distal end of tube outer leg 35c to prevent the volatile material 25 from flowing out of U-shaped outlet tube 35 until the consumer wishes to use the volatile material dispensing device 10. Protective cover 27a is attached to tear-off tab 27. The volatile material dispensing device 10 is activated when the consumer initiates the flow of volatile material 25 by manually removing the protective cover 27a from the end of U-shaped outlet tube 35 by pulling on tear-off tab 27.

Referring now to FIG. 7 and FIG. 8, preferably external housing 11 further comprises an active dispersal mechanism, such as fan 33, with associated support structures, a low voltage power supply and associated wiring to operatively connect fan 33 to the low voltage power supply.

Fan 33 encourages more airflow around and over pad 34 to enable more efficient evaporation of volatile material 25. Fan 33 is provided with necessary support, wiring, and power to be operable. Fan 33 is preferably powered by a low voltage power source, either an ac power source such as a step-down transformer, or, more preferably, a dc power source such as battery 31. For convenience, a single low voltage power source, such as battery 31, may power both fan 33 and motor 41, although two low voltage power sources may optionally be utilized. Support structure 36 (FIG. 7) supports and attaches fan 33 to an inner surface of external housing 11.

Volatile material dispensing device 10 may be freestanding and moveable or may be designed to attach to a vertical surface. To enable convenient wall attachment, a wall attachment member 52 is provided, which is configured to furnish a vertical outward presentation suitable for attaching to a vertical surface, as opposed to the rounded presentation of housing side wall 18. Attachment may be implemented by adhesive means, such as glue or double-sided tape, or mechanical means, such as nails or screws 54.

Though illustrated in a generally cylindrical form, in practice, external housing 11 may be in other geometric forms and may, for example, be oval, hexagonal, or cuboidal.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

I claim:

1. A device for supplying volatile materials to be dispensed into the atmosphere, comprising:
a quantity of volatile material;
a replaceable canister comprising a reservoir and a U-shaped outlet tube, wherein said reservoir has a reservoir interior surface defining a cavity configured to accommodate said quantity of volatile material;

wherein said U-shaped outlet tube comprises a tube inner leg, a tube outer leg, and a tube crosspiece, and wherein said tube inner leg is fluidly connected to a lower area of said reservoir;

wherein said reservoir comprises a reservoir outer wall, a reservoir top wall, and a reservoir bottom wall, and wherein said reservoir outer wall has a degree of flexibility; and an external housing comprising a housing side wall, a housing bottom wall, housing interior surfaces defining a housing interior chamber, and a powered actuating unit, wherein said housing interior chamber is sized and configured to receive said replaceable canister, and wherein said powered actuating unit is configured to apply pressure to said reservoir outer wall.

2. The device for supplying volatile materials to be dispensed into the atmosphere, as recited in claim 1, wherein said external housing further comprises a lid hingedly connected to an upper area of said housing side wall, wherein said lid is configured to allow or to restrict access to said housing interior chamber.

3. The device for supplying volatile materials to be dispensed into the atmosphere, as recited in claim 2, wherein said housing side wall is configured with multiple housing side wall apertures defining air passageways to allow air flow from inside said external housing to the outside of said external housing.

4. The device for supplying volatile materials to be dispensed into the atmosphere, as recited in claim 3, wherein said tube outer leg of said U-shaped outlet tube is open to said atmosphere.

5. The device for supplying volatile materials to be dispensed into the atmosphere, as recited in claim 4, wherein said powered actuating unit comprises an activator positioned against said reservoir outer wall by which said powered actuating unit contacts said reservoir outer wall to apply pressure, a motor, and connective gearing to operatively connect said motor to said activator.

6. The device for supplying volatile materials to be dispensed into the atmosphere, as recited in claim 5, wherein said external housing further comprises a fan mounted in the interior of said external housing.

7. The device for supplying volatile materials to be dispensed into the atmosphere, as recited in claim 5, wherein said powered actuating unit further comprises a low voltage power source electrically connected to said motor for providing electric power to said motor.

8. The device for supplying volatile materials to be dispensed into the atmosphere, as recited in claim 7, wherein said low voltage power source is a battery.

9. The device for supplying volatile materials to be dispensed into the atmosphere, as recited in claim 7, wherein said low voltage power source is a step-down transformer.

10. The device for supplying volatile materials to be dispensed into the atmosphere, as recited in claim 7, wherein said low voltage power source is a solar cell.

11. The device for supplying volatile materials to be dispensed into the atmosphere, as recited in claim 7, wherein said lid further comprises a lid fastener configured to secure said lid to an upper, forward area of said housing side wall, and wherein said housing side wall is substantially cylindrical and said housing bottom wall is substantially circular.

12. The device for supplying volatile materials to be dispensed into the atmosphere, as recited in claim 11, further comprising a wall attachment member configured to allow attachment of said device for supplying volatile materials to a vertical surface.

13. The device for supplying volatile materials to be dispensed into the atmosphere, as recited in claim 12, wherein said quantity of volatile material comprises at least two volatile materials.

14. The device for supplying volatile materials to be dispensed into the atmosphere, as recited in claim 13, wherein the pressure applied to said reservoir outer wall by said activator causes a portion of said quantity of volatile material to flow up said tube inner leg and across said tube crosspiece to enter said tube outer leg.

15. The device for supplying volatile materials to be dispensed into the atmosphere, as recited in claim 14, further comprising an absorbent pad disposed under said tube outer leg of said U-shaped outlet tube 35 and configured to receive said portion of said quantity of volatile material exiting from said tube outer leg.

16. The device for supplying volatile materials to be dispensed into the atmosphere, as recited in claim 15, wherein said absorbent pad is connected to said replaceable canister.

17. The device for supplying volatile materials to be dispensed into the atmosphere, as recited in claim 15, wherein said absorbent pad is connected to said external housing.

18. The device for supplying volatile materials to be dispensed into the atmosphere, as recited in claim 15, wherein said quantity of volatile material comprises scented oil.

19. The device for supplying volatile materials to be dispensed into the atmosphere, as recited in claim 15, wherein said quantity of volatile material comprises a disinfectant.

20. A device for supplying volatile materials for distribution in the atmosphere, comprising:

a supply of at least one volatile material;

a replaceable canister comprising a reservoir and a U-shaped outlet tube, wherein said reservoir has a reservoir interior surface defining a cavity configured to accommodate said supply of at least one volatile material, and wherein said U-shaped outlet tube comprises a tube inner leg, a tube outer leg, and a tube crosspiece, and wherein said tube inner leg is connected to a lower area of said reservoir and is in fluid communication with said cavity defined by said reservoir interior surface, and wherein said tube outer leg of said U-shaped outlet tube is open to said atmosphere;

wherein said reservoir comprises a reservoir outer wall, a reservoir top wall, and a reservoir bottom wall, and wherein said reservoir outer wall has a degree of flexibility; and an external housing comprising a generally cylindrical housing side wall, a generally circular housing bottom wall, housing interior surfaces defining a housing interior chamber, comprises a lid hingedly connected to an upper area of said housing side wall, and a powered actuating unit, wherein said housing interior chamber is sized and configured to receive said replaceable canister, and wherein said powered actuating unit is configured to apply pressure to said reservoir outer wall.

21. The device for supplying volatile materials for distribution in the atmosphere, as recited in claim 20, wherein:

said powered actuating unit comprises an activator configured to apply pressure to the reservoir outer wall, a motor, connective gearing to operatively connect said motor to said activator, and a low voltage power source electrically connected to said motor for providing electric power to said motor;

wherein said housing side wall is configured with multiple housing side wall apertures defining air passageways to allow air flow from inside said external housing to the outside of said external housing;

wherein said external housing further comprises a fan powered by said low voltage power source; and wherein said device for supplying volatile materials for distribution in the atmosphere comprises an absorbent pad positioned under said tube outer leg.

22. The device for supplying volatile materials for distribution in the atmosphere, as recited in claim 21, wherein said low voltage power source is a battery.

23. The device for supplying volatile materials to be dispensed into the atmosphere, as recited in claim 21, wherein said absorbent pad is connected to said replaceable canister.

24. The device for supplying volatile materials to be dispensed into the atmosphere, as recited in claim 21, wherein said absorbent pad is connected to said external housing.

* * * * *